Figure 2:
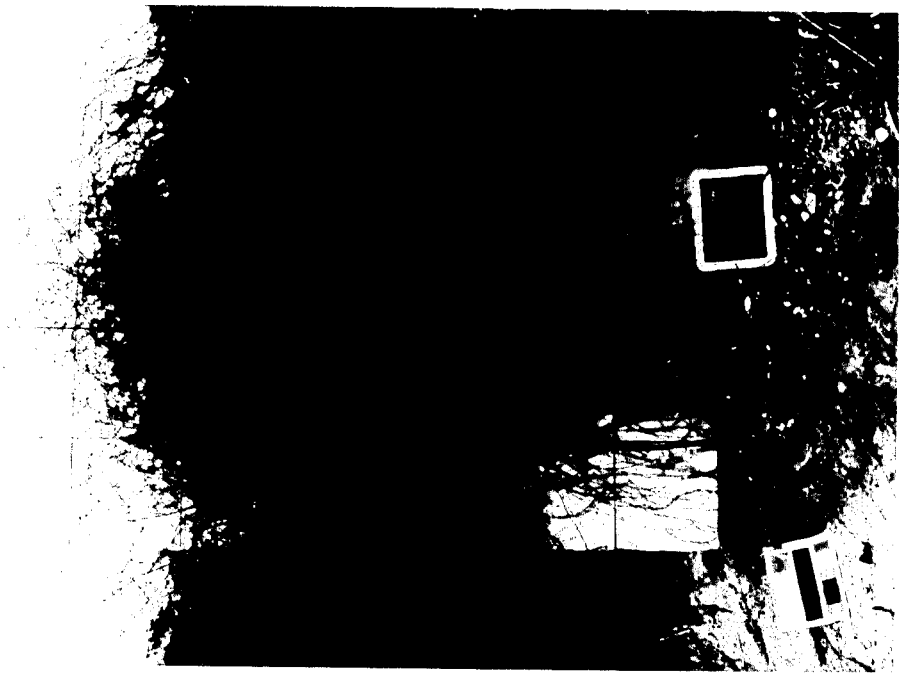

United States Patent [19]

Ellison et al.

[11] Patent Number: Plant 7,311

[45] Date of Patent: Aug. 28, 1990

[54] ASPARAGUS PLANT

[75] Inventors: J. Howard Ellison, Milltown; John J. Kinelski, Princeton, both of N.J.

[73] Assignee: Rutgers University, New Brunswick, N.J.

[21] Appl. No.: 392,421

[22] Filed: Aug. 11, 1989

[51] Int. Cl.[5] ..... A01H 5/00

[52] U.S. Cl. ..... Plt./89

[58] Field of Search ..... Plt./89

*Primary Examiner*—James R. Feyrer

*Attorney, Agent, or Firm*—Frank B. Robb

[57] ABSTRACT

A cloned variety of female Asparagus plant embodying great uniformity of all characteristics which include vigor, rust tolerance, yielding of a high proportion of large "jumbo" spears, maintaining good plant stand, resistance to crown rot under adverse low, wet field conditions and superior volume of quality spears.

2 Drawing Sheets

This invention relates to a new and distinct variety of cloned Asparagus plant which is one of the products of a detailed, carefully planned program of development of asparagus in general.

The several objects of our program embrace all the areas of improvement we can produce, including resistance to rust or tolerance thereto, and crown rot resistance, increased vigor and high yield of uniform large spears, the largest being the so called "jumbo" spears.

The instant cloned variety embraces all the improvements desired as outlined above together with uniformity and high yield of the large "jumbo" spears.

We have chosen to denominate this new cloned variety as "Jersey Queen" being a real giant female Asparagus plant and have caused the same to be asexually propagated by crown division and by tissue culture as well.

We have found that the desirable characteristics referred to above have in fact been fixed through successive generations with consistent uniformity, the good plant stand and vigor providing definite contrast with clones on either side of "Jersey Queen" which have died of crown rot in a low wet portion of an experimental field.

This new plant was selected for its desirable characteristics, grown and tested in an old field of "Mary Washington" Asparagus, and unpatented variety, long a standard in the industry. The oil field was located on the eastern shore of Maryland.

The high yield is emphasized by noting that this cloned variety yields nearly 300% of the yield of other hybrid varieties per acre which is emphasized in data supplied herewith.

"Jersey Queen" produces 90% jumbo spears, weighing about twice as much as medium spears and since hybrid varieties generally produce only 30–40% jumbo spears, "Jersey Queen" is much less expensive to harvest per pound, even though asparagus spears are hand harvested, weight being an important commercial factor.

In the plant data set forth below in detail, further distinctions are set forth and summarized, which assist in distinguishing the instant cloned variety from others which we have developed in a long continuing breeding program to establish and maintain the best characteristics of Asparagus plants and enable them to produce under widely varying conditions.

Figure 1:
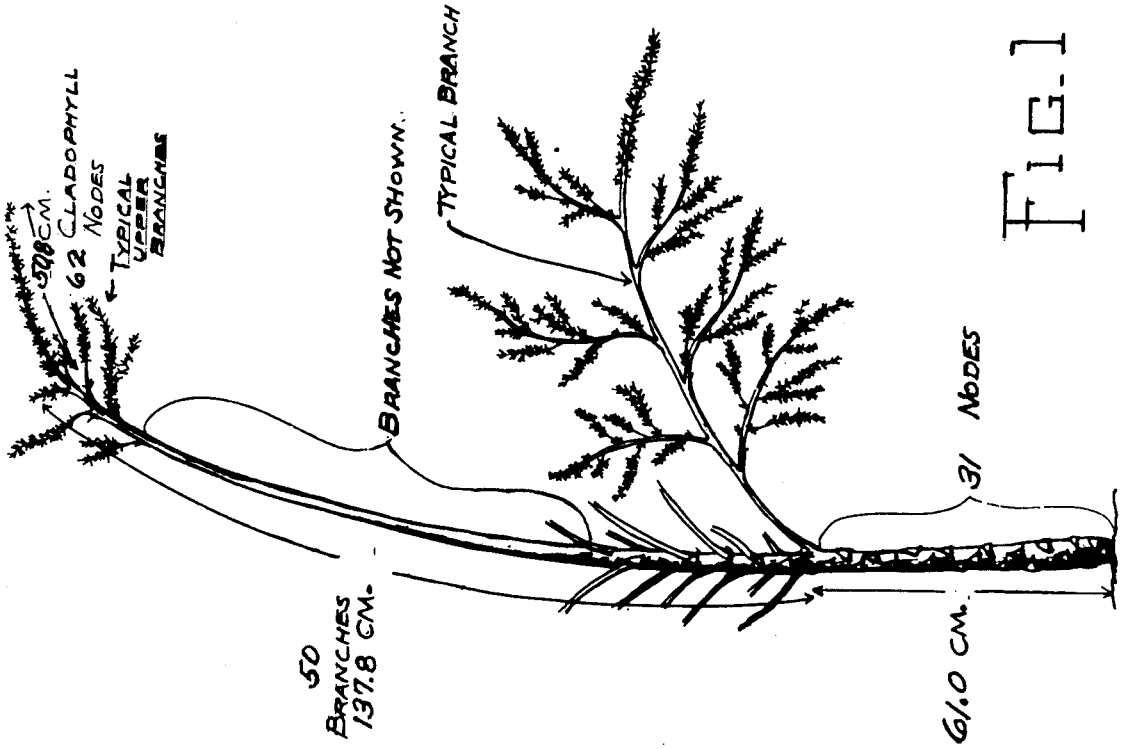

We have shown in the drawing in FIG. 1, certain of the data applied to a plant described, and in FIG. 2 show in color as nearly representative of that of the actual plant as is possible in a color reproduction of this character, the color designations where furnished referring to Munsell Color Cascade by MacBeth Color Division, Baltimore, Md.

ASPARAGUS PLANT DATA

ASPARAGUS PLANT "JERSEY QUEEN"
Note, the indication "(1)" below, indicates specifications of the largest stalk (Md 10 clone)

| | |
|---|---|
| STALK DATA | |
| Number of nodes below first branch (1) | 31 |
| Number of cm from crown to first branch (1) | 61.0 |
| Number of branches (1) | 50 |
| Number cm between first and last branch (1) | 137.8 |
| Internode length in cm between branches (1) | 2.75 |
| Number of cladophyll nodes beyond last branch (1) | 62. |
| Number of cm beyond last branch (1) | 50.8 |
| Internode length in cm beyond last branch (1) | 0.82 |
| Largest stalk diameter in mm | 28.0 |
| Mean diameter of three largest stalks in mm | 26.2 |
| Number of stalks | 33 |
| Stalk vigor index | 22,653 |
| Mature stalk color, bloom removed. Color No. (1) | 22-13 |
| Crown to first branch of highest headed stalk cm | 77.5 |
| Length of highest headed stalk cm | 242.6 |
| FLOWER DATA | |
| Petal tip (yellow) Color No. (1) | 25-4 |
| Petal base (green) Color No. (1) | 23-11 |
| Flower length mm | 4.0 |
| Flower width at midpoint mm | 2.1 |
| FRUIT DATA (Md 10 × 22-8) | |
| Weight of 100 fruit (g) | 18.6 |
| Water displacement of 100 fruit (ml) | 19.0 |
| Number of seed per 100 fruit | 253 |
| Weight of seed per 100 fruit (g) | 7.3 |
| Mean weight per seed | 0.0289 |
| Water displacement of seed of 100 fruit (ml) | 8.0 |
| Mature fruit Color No. (1) | 33-12 |
| CLADOPHYLL DATA | |
| Number per node | 2.83 |
| Length (mm) | 18.75 |
| Width (mm) | 0.133 |

We claim:

1. A new and distinct cloned variety of female Asparagus plant substantially as shown and described, characterized particularly as to novelty by the outstanding vigor and rust tolerance, yield of high proportion of large "jumbo" spears, which weight nearly twice as much as medium spears of varieties which produce only 30–40% jumbo spears, ability to maintain good plant stand and vigor under conditions which usually result in serious crown rot, and consistently maintaining these desirable characteristics over large quantities of Asparagus plants.

* * * * *